US012723902B2

(12) United States Patent
Boschert et al.

(10) Patent No.: US 12,723,902 B2
(45) Date of Patent: *Sep. 1, 2026

(54) SYSTEM AND METHOD FOR MONITORING STORAGE CONDITIONS WITHIN CONTAINERS

(71) Applicant: Rolls-Royce Corporation, Indianapolis, IN (US)

(72) Inventors: Jason Boschert, Indianapolis, IN (US); Michael Patrick Verdicchio, Indianapolis, IN (US); Allen Brian Barta, Indianapolis, IN (US); Cory Alfred Nation, Indianapolis, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 992 days.

This patent is subject to a terminal disclaimer.

(21) Appl. No.: 17/733,529

(22) Filed: Apr. 29, 2022

(65) Prior Publication Data

US 2022/0260395 A1 Aug. 18, 2022

Related U.S. Application Data

(63) Continuation of application No. 16/173,772, filed on Oct. 29, 2018, now Pat. No. 11,326,909.

(51) Int. Cl.

| | |
|---|---|
| ***G01D 21/02*** | (2006.01) |
| ***G01D 9/00*** | (2006.01) |

(Continued)

(52) U.S. Cl.

CPC ............ *G01D 21/02* (2013.01); *G01D 9/005* (2013.01); *G01D 11/30* (2013.01);

(Continued)

(58) Field of Classification Search

CPC ........ G01D 11/30; G01D 9/005; G01D 21/02; G01M 13/00; G01M 15/00; G01N 33/0075

(Continued)

(56) References Cited

U.S. PATENT DOCUMENTS

| | | | | |
|---|---|---|---|---|
| 2,674,371 A * | 4/1954 | Blackinton | ............... | F02C 7/00 206/319 |
| 5,481,245 A | 1/1996 | Moldavsky | | |

(Continued)

FOREIGN PATENT DOCUMENTS

| | | | |
|---|---|---|---|
| DE | 102020204696 A1 * | 10/2020 | ......... G01L 19/0038 |
| JP | 2003279217 A * | 10/2003 | |

(Continued)

*Primary Examiner* — Laura Martin
*Assistant Examiner* — Nashmiya S Fayyaz
(74) *Attorney, Agent, or Firm* — Barnes & Thornburg

(57) ABSTRACT

Systems and methods are presented for monitoring shipping containers. A system comprises a shipping container, a sensing component, and a transmission device. The shipping container defines an interior compartment. The sensing component is positioned within the interior compartment and comprises one or more sensors, a sensing component battery, a sensing component microcontroller, and a communication chip. The one or more sensors sense atmospheric data. The sensing component microcontroller has a memory and receives the atmospheric data sensed by the one or more sensors at a predetermined interval and stores the atmospheric data in the memory. The transmission device is external to the interior compartment and comprises a receiver and a transmitter. The receiver receives data transmitted by the sensing component. The transmitter transmits the received data to a storage location. The transmission device is paired with the sensing component or an interior component contained within the interior compartment.

18 Claims, 5 Drawing Sheets

(51) Int. Cl.

| | |
|---|---|
| ***G01D 11/30*** | (2006.01) |
| ***G01N 33/00*** | (2006.01) |
| *G01M 13/00* | (2019.01) |
| *G01M 15/00* | (2006.01) |

(52) U.S. Cl.
CPC ......... *G01N 33/0075* (2013.01); *G01M 13/00* (2013.01); *G01M 15/00* (2013.01)

(58) Field of Classification Search
USPC ........................................................ 73/865.8
See application file for complete search history.

(56) References Cited

U.S. PATENT DOCUMENTS

| | | | | |
|---|---|---|---|---|
| 6,512,455 | B2 | 1/2003 | Finn et al. | |
| 7,265,668 | B1 | 9/2007 | Brosius | |
| 8,047,432 | B2 | 11/2011 | Breed | |
| 8,620,343 | B1 | 12/2013 | Lau et al. | |
| 8,994,546 | B2 | 3/2015 | Breed et al. | |
| 9,689,824 | B2 | 6/2017 | Le Neel et al. | |
| 2005/0073406 | A1 | 4/2005 | Easley et al. | |
| 2007/0096920 | A1* | 5/2007 | Cargonja | G08B 25/10 340/572.8 |
| 2011/0193710 | A1 | 8/2011 | McIlvain et al. | |
| 2015/0177094 | A1 | 6/2015 | Friedlander et al. | |
| 2015/0205308 | A1 | 7/2015 | Huat | |
| 2018/0018618 | A1 | 1/2018 | Groseclose | |
| 2022/0348400 | A1* | 11/2022 | Pham | B65D 90/48 |

FOREIGN PATENT DOCUMENTS

| | | | | | |
|---|---|---|---|---|---|
| RU | 173363 | U1 | * | 8/2017 | |
| WO | WO-2009070754 | A1 | * | 6/2009 | G08B 13/2491 |
| WO | WO-2009130586 | A2 | * | 10/2009 | F01D 25/285 |

* cited by examiner 1540
1500
1570
Power Connector
1530
Transmission Device Microcontroller
1580
Ethernet Port
1550
Onboard Memory Component
1510
Receiver
1560
Transmission Device Battery
1520
Transmitter
Mounting Component
1450

SYSTEM AND METHOD FOR MONITORING STORAGE CONDITIONS WITHIN CONTAINERS

PRIORITY CLAIM

This application is a continuation of U.S. patent application Ser. No. 16/173,772, filed Oct. 29, 2018, which is entirely incorporated by reference.

BACKGROUND

Availability rates of complex machinery such as aircraft can be dependent upon the effectiveness of the shipping containers used to transport major components such as aircraft engines, which protect the asset during transport. The availability of other components such as weapons, engine subsystems like compressors and gearboxes, and other high value assets depends on the effectiveness of their shipping containers as well. Shipping containers, such as those for aircraft engines, also provide for long term storage in uncertain environments. The goal of these containers is to maintain adequate conditions on the interior of the containers to prevent any damage to the aircraft engine or other component caused by atmospheric conditions or movement during transport. However, these containers do not always succeed in protecting the engines and other components from the elements or shock due to aggressive movement of the container. There have been numerous cases of container humidity levels exceeding specifications, or rough handling during transport, which result in the necessity of unplanned engine repairs. These engine repairs may affect aircraft availability and are costly.

SUMMARY

According to some aspects of the present disclosure, a system is disclosed for monitoring shipping containers. The system comprises a shipping container, a sensing component, and a transmission device. The shipping container defines an interior compartment. The sensing component is positioned within the interior compartment. The sensing component comprises one or more sensors, a sensing component battery, a sensing component microcontroller, and a communication chip. The one or more sensors are for sensing atmospheric data. The sensing component microcontroller has a memory and receives the atmospheric data sensed by the one or more sensors at a predetermined interval and stores the atmospheric data in the memory. The transmission device is external to the interior compartment defined by the shipping container. The transmission device comprises a receiver and a transmitter. The receiver is for receiving data transmitted by the sensing component. The transmitter is for transmitting the received data to a storage location. The transmission device is paired with the sensing component or an interior component contained within the interior compartment.

In some embodiments, the one or more sensors include one or more of temperature, humidity, shock, or light sensing capabilities. In some embodiments, the transmission device is mounted on the exterior of the shipping container. In some embodiments, the transmission device further comprises a transmission device microcontroller, one or more transmission device antennas, an onboard memory component, and a transmission device battery. The transmission device microcontroller is for processing the received data. The one or more transmission device antennas are for wireless communication. The onboard memory component is for storage of the received data.

In some embodiments, the transmission device is a smartphone or an internet-connected device. In some embodiments, the shipping container includes one or more rails equipped to secure the interior component within the interior compartment, and the sensing component is mounted on a rail.

In some embodiments, the shipping container comprises two removably coupled portions. In some embodiments, the sensing component is mounted on a first portion, and the transmission device is mounted on a second portion. In some embodiments, the sensing component or transmission device is mounted by a magnet, suction cup-like fixture, or bracket with a threaded connection. In some embodiments, the shipping container is hermetically sealed.

In some embodiments, the storage location is a cloud storage location. In some embodiments, the interior component is an engine, engine subsystem, or weapon.

In some embodiments, the transmission device is configured to query the sensing component to effect transmission of atmospheric data. In some embodiments, the sensing component periodically transmits atmospheric data to the transmission device.

According to further aspects of the present disclosure, a method is disclosed for monitoring the environment within an interior compartment defined by a shipping container. The method comprises positioning a sensing component within the compartment; sensing one or more environmental conditions within the compartment by the sensing component; positioning a transmitting component proximate the shipping container and external to the compartment; and transferring data related to the one or more environmental conditions between the sensing component and the transmitting component.

In some embodiments, the method further comprises transmitting a query from the transmitting component to the sensing component, and responsive to the query, transferring data related to the one or more environmental conditions from the sensing component to the transmitting component. In some embodiments, the query is transmitted on a predetermined schedule. In some embodiments, the transmitting component stores the data. In some embodiments, the transmitting component transmits the data to a receiver remote from the transmitting component.

In some embodiments, the method further comprises transferring data between the sensing component and the transmitting component by wireless communication. In some embodiments, the data is related to one or more of temperature, humidity, movement, and light.

BRIEF DESCRIPTION OF THE DRAWINGS

The following will be apparent from elements of the figures, which are provided for illustrative purposes.

Figure 1:
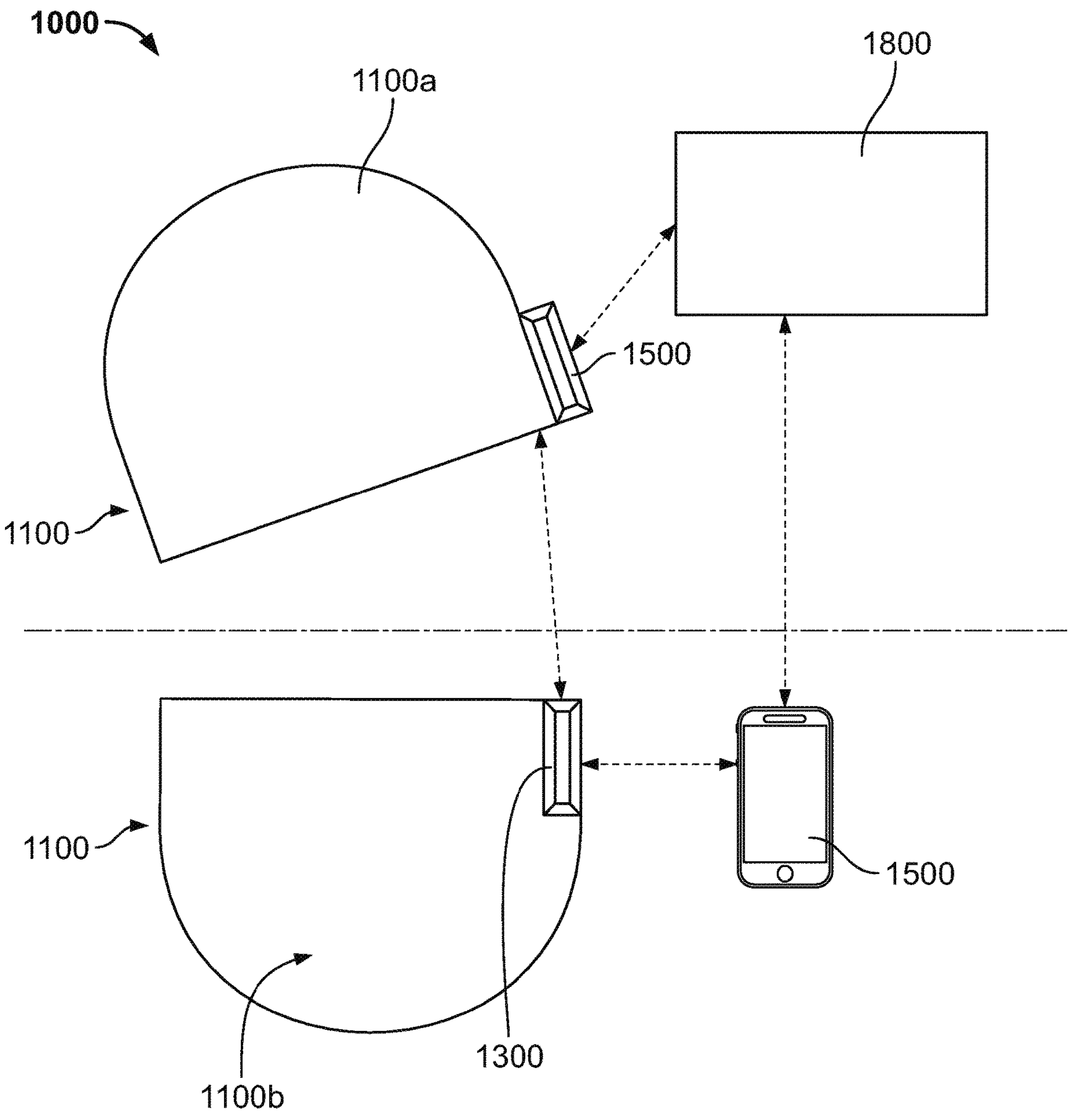
FIG. 1 is a schematic view of a system for monitoring environmental conditions within shipping containers, in accordance with some embodiments of the present disclosure.

The present application discloses illustrative (i.e., example) embodiments. The claimed inventions are not limited to the illustrative embodiments. Therefore, many implementations of the claims will be different than the illustrative embodiments. Various modifications can be made to the claimed inventions without departing from the spirit and scope of the disclosure. The claims are intended to cover implementations with such modifications.

DETAILED DESCRIPTION

For the purposes of promoting an understanding of the principles of the disclosure, reference will now be made to a number of illustrative embodiments in the drawings and specific language will be used to describe the same.

There is a need to remotely monitor the environmental conditions within shipping containers that house aircraft engines, engine subsystems, weapons, and other high-value assets on a regular basis to prevent damage to the interior component or to detect conditions which may have damaged the interior component. The present disclosure is directed to systems and methods of monitoring environmental conditions in shipping containers. The present disclosure improves upon prior art systems and methods by employing a sensing component inside the shipping container to monitor environmental conditions and an external transmission device paired with the interior component or sensing component and capable of automatically transmitting sensory data and data analytics to various storage locations. The present disclosure facilitates proactive asset monitoring, reducing the probability of unplanned repairs to interior components.

In some embodiments of the present disclosure, a system for monitoring shipping containers 1000 is used to monitor conditions within the interior compartment 1150 of an aircraft engine shipping container 1100. While this embodiment shows system 1000 being used to monitor an aircraft engine shipping container 1100, the system 1000 may be used on other containers housing components such as engine subsystems, weapons, or other high value assets. FIG. 1 is a schematic view of a system for monitoring shipping containers 1000. The aircraft engine shipping container 1100 may comprise two removably coupled portions 1100*a* and 1100*b*. The two portions 1100*a* and 1100*b* may be decoupled in order to place an engine 1200 (shown in FIG. 4) within the interior compartment 1150 formed by coupling portions 1100*a* and 1100*b*. The two portions 1100*a* and 1100*b* may be coupled together and hermetically sealed to protect the engine from exposure to variable atmospheric conditions surrounding the container 1100. A sensing component 1300 may be mounted within the interior compartment 1150 formed by the aircraft engine shipping container 1100 via a mounting component 1400 (shown in FIG. 2). The sensing component 1300 monitors conditions within the interior compartment 1150 formed by aircraft engine shipping container 1100 by collecting sensor data through a variety of sensors 1310 (detailed in FIG. 2). The sensing component may generate encrypted data from the sensor data prior to communicating the data to other devices.

A transmission device 1500 may be located external to the aircraft engine shipping container 1100. The transmission device 1500 may be mounted to the exterior of the aircraft engine shipping container 1100 by conventional means. The transmission device 1500 and sensing component 1300 may be mounted on separate portions 1100*a* and 1100*b*. This may allow the sensing component 1300 to monitor whether the aircraft engine shipping container 1100 has been opened, i.e., whether the portions 1100*a* and 1100*b* have been physically separated. The devices may be mounted by conventional means including strong magnets, suction cup-like fixtures, or a bracket with a threaded connection such as a bolt. If threaded mounting materials such as bolts are used to mount sensing component 1300 and transmission device 1500, the sensing component 1300 and transmission device 1500 could be connected to each other using the same mounting materials, and wiring may be passed from the sensing component 1300 to the transmission device 1500. The mounting and connection holes may be weatherproof and sealed to prevent excess moisture in the container. The data may also be captured by a smartphone or internet-connected device proximate the aircraft engine shipping container 1100.

The transmission device 1500 may poll the sensing component 1300 on a specified frequency in order to obtain the sensed and/or recorded data. In some embodiments, the sensing component 1300 may periodically transmit data to the transmission device 1500. The sensing component 1300 may communicate the data (which may be encrypted) a short distance through the walls of the aircraft engine shipping container 1100 to a transmission device 1500. The transmission device 1500 may transmit the data via a cellular network, Wi-Fi connection, satellite, or hard-wired cabling such as USB or an Ethernet line to a storage location 1800. This transmission may occur at any desired frequency, such as hourly, daily, weekly, etc. The storage location 1800 may be a military-grade secure cloud storage location. The storage location 1800 may be an on-premise storage location. The storage location 1800 may be locked behind a firewall with least-privilege user security.

In order to ensure the data is only collected by known hosts, the transmission device 1500 may be paired with the sensing component 1300 or the serial number of the engine 1200. The sensing component 1300 may be password protected. This may prevent unwanted third parties from accessing the sensor data via a smartphone or internet-connected devices.

Figure 2:
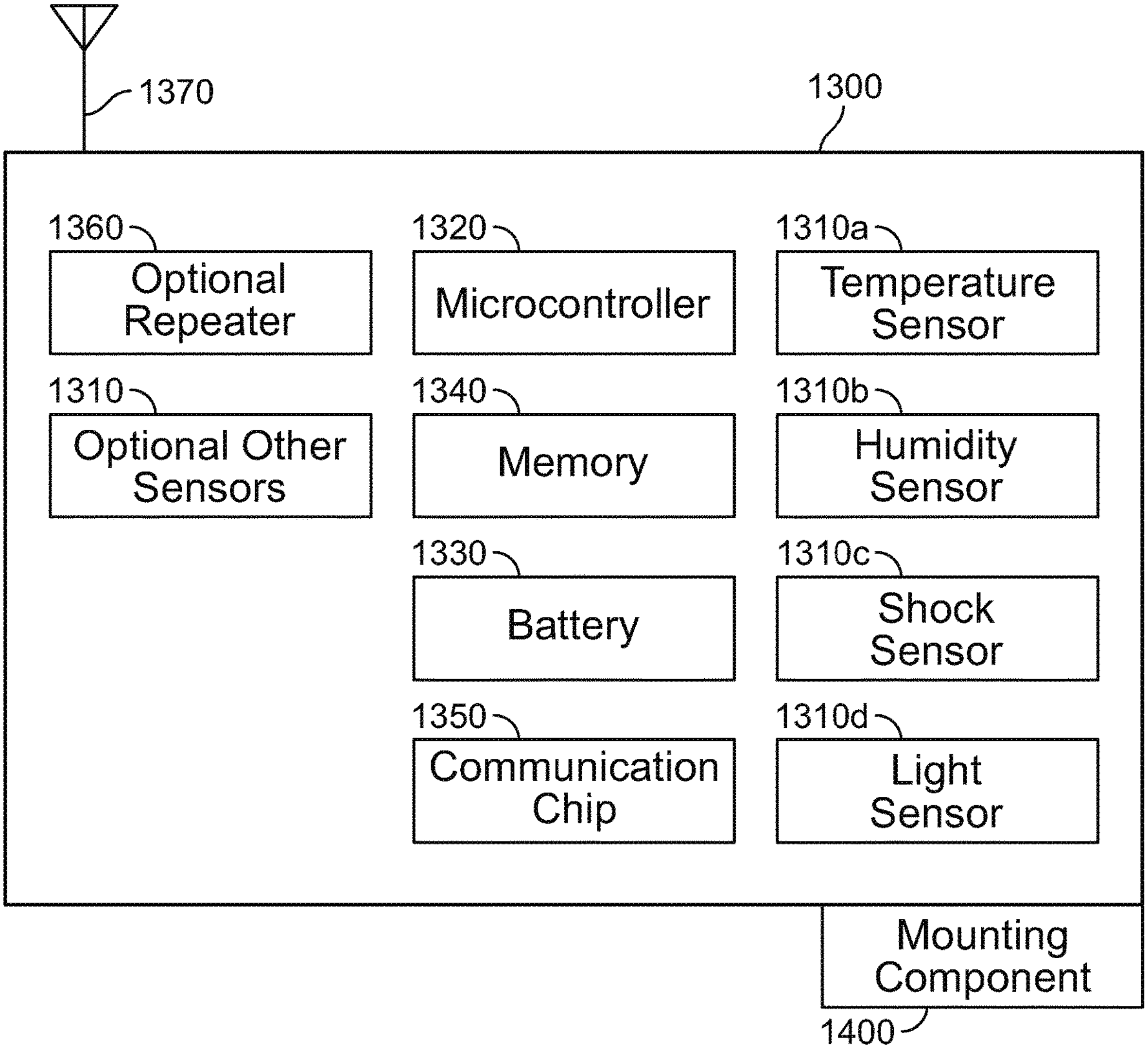
FIG. 2 is a schematic view of a sensing component, in accordance with some embodiments of the present disclosure.

FIG. 2 is a schematic view of the sensing component 1300. The sensing component 1300 may include various sensors 1310, for example, temperature sensor 1310*a*, humidity sensor 1310*b*, shock sensor 1310*c*, light sensor 1310*d*, and other sensors 1310. These sensors 1310 may be used to collect data on various atmospheric conditions such as temperature and humidity, or data on the physical movement of the container such as a potentially damaging physical shock from dropping the container. The sensing component 1300 may comprise a small box mounted to the interior of the aircraft engine shipping container 1100 via a mounting component 1400. The sensing component 1300 may be mounted directly on the rails 1900 (shown in FIG. 4) of the aircraft engine shipping container 1100. In some embodiments, the sensing component 1300 may be mounted on the walls of the aircraft engine shipping container 1100. Mounting component 1400 may include various conventional mounting materials described above.

The sensing component 1300 may further comprise a microcontroller 1320 and a battery 1330 to power the sensing component 1300. The microcontroller 1320 may be used to take measurements at a specified frequency and store sensor data in a memory 1340. The memory 1340 may be RAM or flash memory. The battery 1330 may be replaceable. The sensor data may be encrypted upon storage in the memory 1340 to generate encrypted data. The sensor data may be encrypted using a secure military-grade encryption standard.

The sensing component 1300 may further comprise a communication chip 1350 for communication with external devices over short distances. The communication chip 1350 may use Near Field Communication (NFC) or Bluetooth Low Energy to securely communicate the encrypted data to the transmission device 1500. The transmission device 1500 may be paired with the sensing component 1300 or a serial number specific to the engine housed within aircraft engine shipping container 1100 to ensure data security. The sensing component 1300 may also include an optional repeater 1360 or an optional antenna 1370 to aid in communication through the walls of the aircraft engine shipping container 1100. The need for an optional repeater 1360 and optional antenna 1370 will depend on the material and thickness of the walls of the aircraft engine shipping container 1100.

Figure 3A:
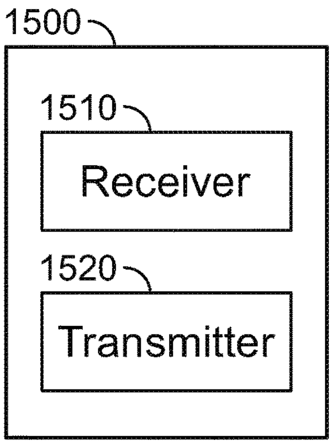
FIG. 3A is a schematic view of a transmission device, in accordance with some embodiments of the present disclosure.

In some embodiments, a transmission device 1500 proximate the aircraft engine shipping container 1100 may be used to transmit encrypted data to a storage location 1800. FIG. 3A is a schematic view of a transmission device 1500 according to some embodiments. The transmission device 1500 may poll the sensing component 1300 on a specified frequency to collect data from the interior compartment 1150 formed by the aircraft engine shipping container 1100. The transmission device 1500 may comprise a receiver 1510 and a transmitter 1520. The communication chip 1350 of the sensing component 1300 may communicate encrypted data to the receiver 1510 upon being polled. The transmitter 1520 may transmit the encrypted data, using the same encryption standard as the sensing component 1300, to a storage location 1800 via a cellular network, Wi-Fi connection, satellite, or hard-wired line such as USB or Ethernet line. The storage location 1800 may be a military-grade secure cloud storage location or an on-premise storage location. The transmission device 1500 may poll data from the sensing component 1300 and immediately transmit the data to a storage location 1800 without storing the data.

Figure 3B:
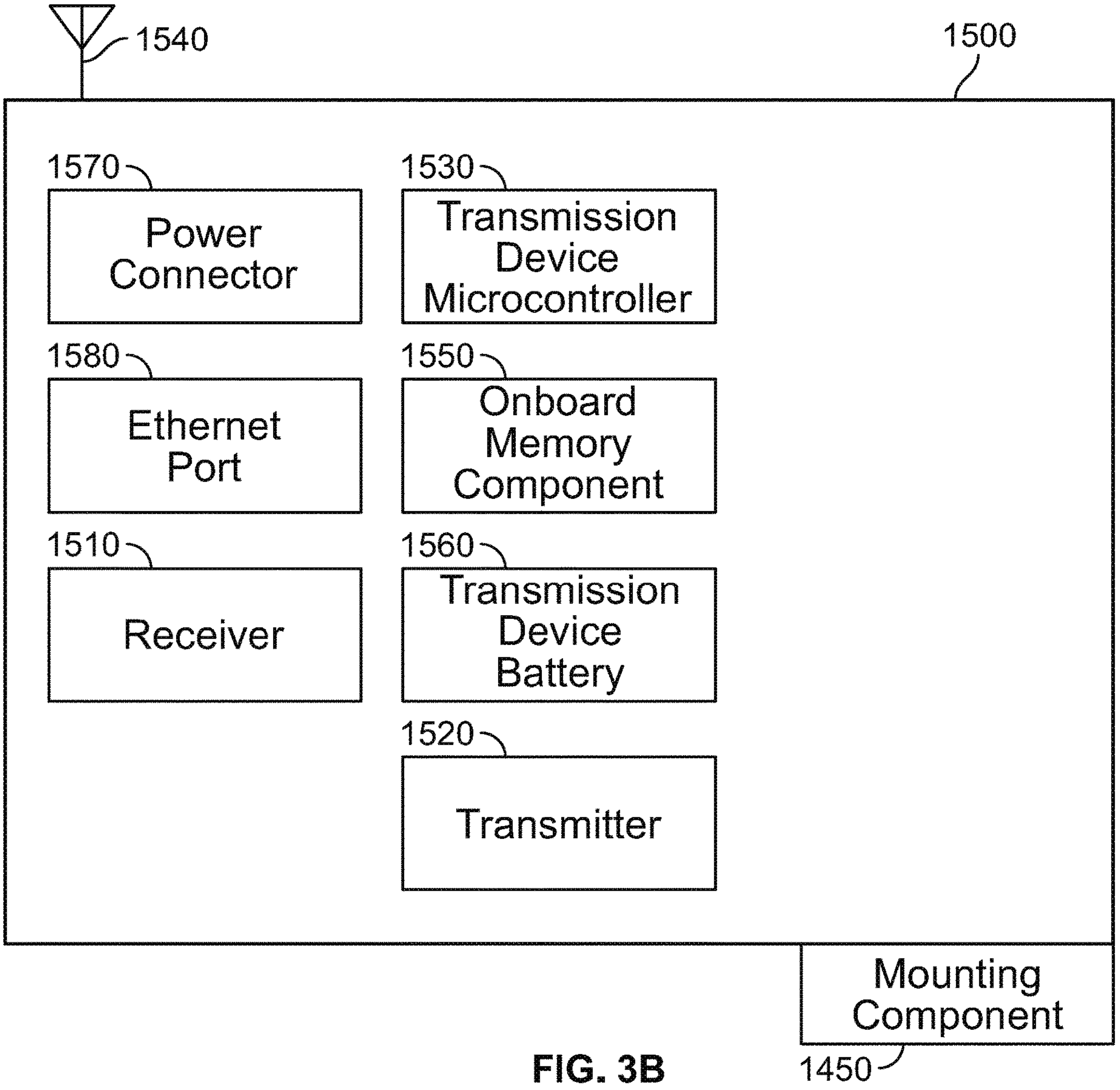
FIG. 3B is a schematic view of a transmission device, in accordance with some embodiments of the present disclosure.

In some embodiments as illustrated in FIG. 3B, the transmission device 1500 may include the functionalities of the transmission device 1500 of FIG. 3A with additional components. The transmission device 1500 may comprise a receiver 1510 and a transmitter 1520. The transmission device 1500 may further comprise a transmission device microcontroller 1530 for processing the encrypted data, a transmission device antenna 1540 for wireless communication, an onboard memory component 1550 for temporary storage, a mounting component 1450, and a transmission device battery 1560. The onboard memory component 1550 may temporarily store data in either RAM or flash memory. The transmission device battery 1560 may be replaceable or rechargeable. Depending on the model, the transmission device 1500 may further comprise a power connector 1570 and Ethernet port 1580.

A smartphone or internet-connected device registered to the sensing component 1300 may also be useful as a transmission device 1500.

Figure 4:
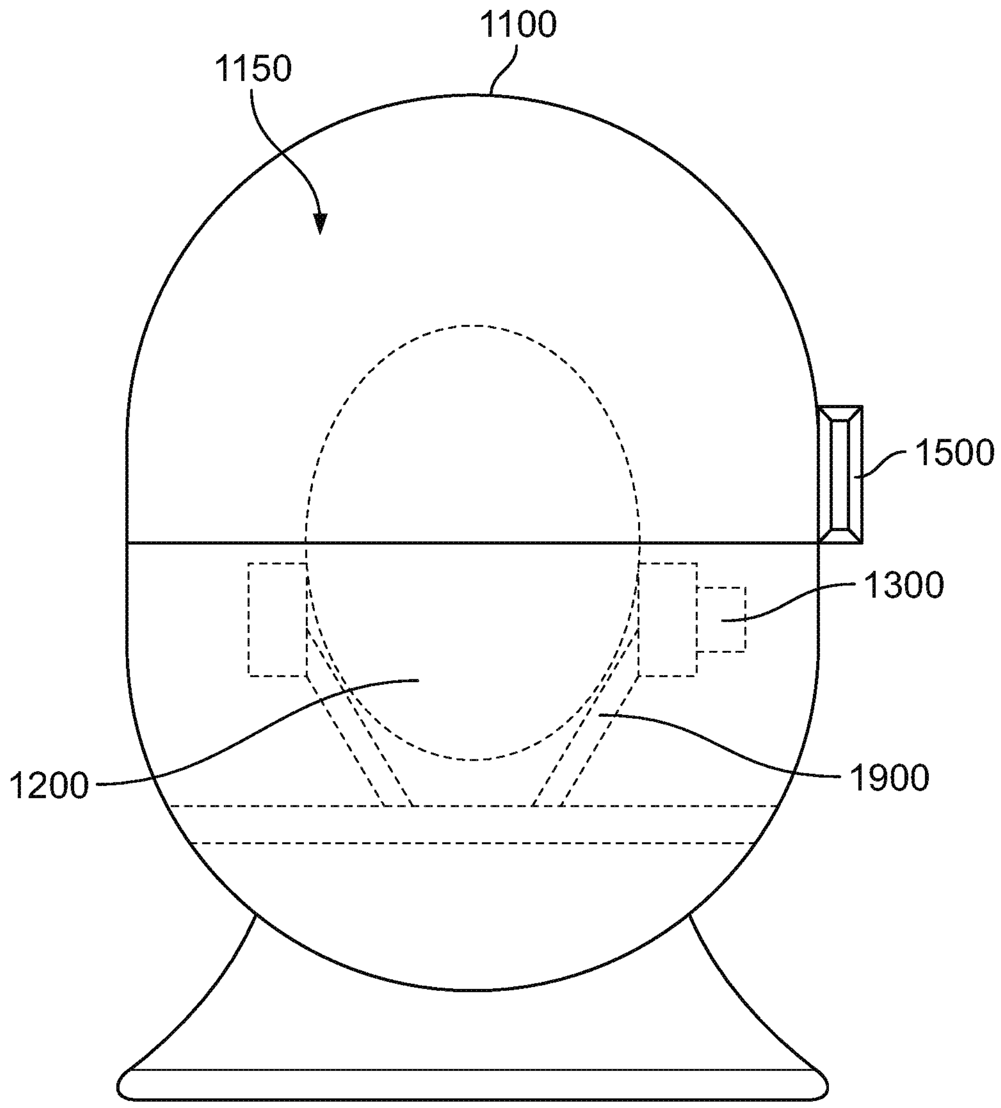
FIG. 4 is a schematic view of an aircraft engine shipping container housing an engine, in accordance with some embodiments of the present disclosure.

FIG. 4 is a schematic view of an embodiment of aircraft engine shipping container 1100 containing an engine 1200. The aircraft engine shipping container 1100 may be hermetically sealed. The sensing component 1300 may be mounted directly on the rails 1900 that secure the engine 1200 in place, allowing the sensing component 1300 to sense the physical shock experienced by the engine. Transmission device 1500 is shown to be mounted on the exterior of the aircraft engine shipping container 1100. In some embodiments, transmission device 1500 may also be proximate to but not mounted on the aircraft engine shipping container 1100.

Figure 5:
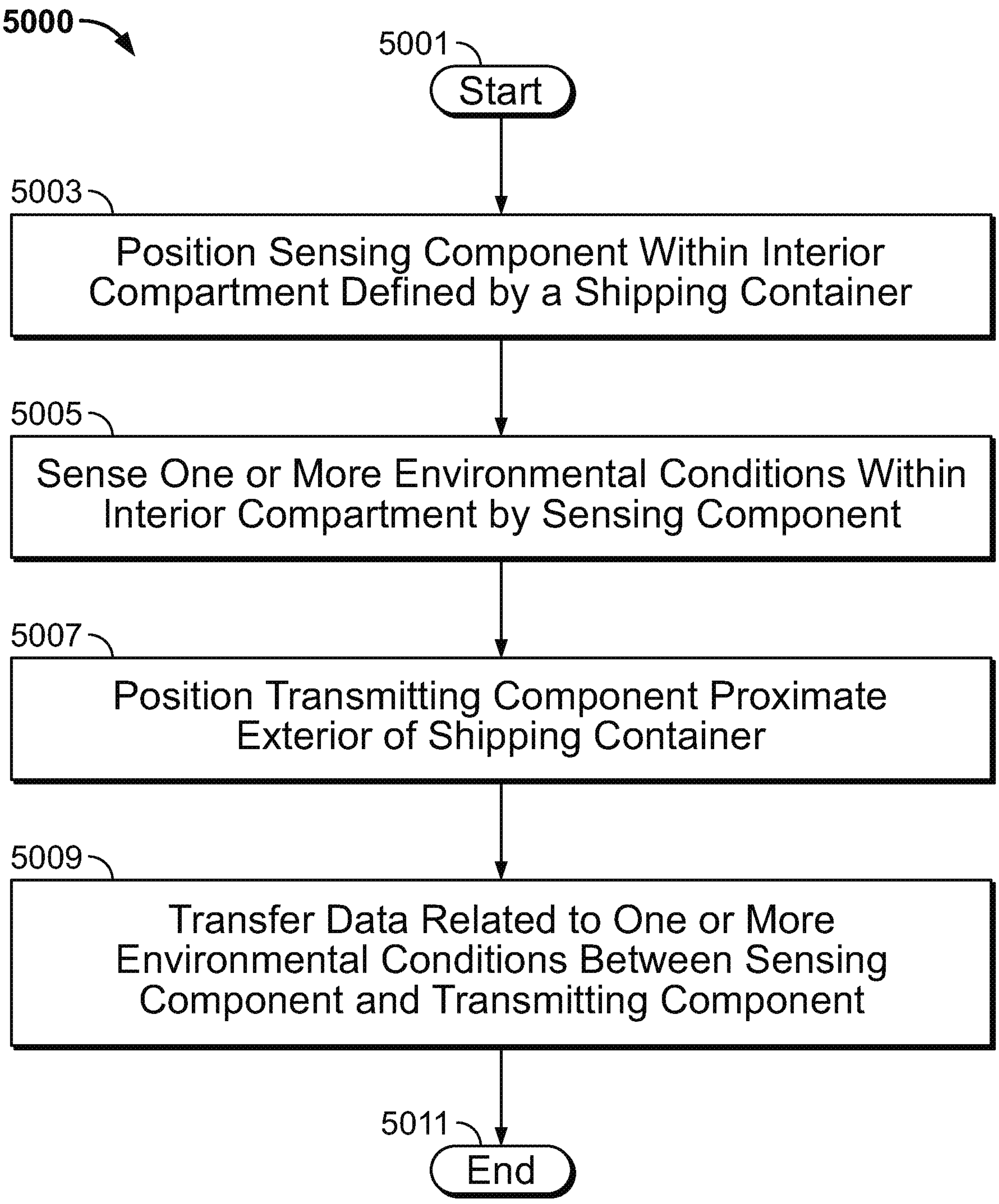
FIG. 5 is a flow diagram of a method in accordance with some embodiments of the present disclosure.

FIG. 5 is a flow diagram of a method for monitoring the environment within an interior compartment defined by a shipping container. Method 5000 begins at Block 5001.

At Block 5003, a sensing component may be positioned within the interior compartment.

At Block 5005, one or more environmental conditions may be sensed within the interior compartment by the sensing component.

At Block 5007, a transmitting component may be positioned proximate the shipping container and external to the compartment. The transmitting component may store data related to one or more environmental conditions. The data related to one or more environmental conditions may be related to one or more of temperature, humidity, movement, and light. The transmitting component may transmit data to a receiver remote from the transmitting component.

At Block 5009, data related to the one or more environmental conditions may be transferred between the sensing component and the transmitting component. Data may be transferred between the sensing component and the transmitting component by wireless communication. A query may be transmitted from the transmitting component to the sensing component. Responsive to the query, data related to the one or more environmental conditions may be transferred from the sensing component to the transmitting component. The query may be transmitted on a predetermined schedule.

Method 5000 ends at Block 5011. Method 5000 enables proactive monitoring of the environment within shipping containers, thereby preventing damage to interior components due to unpredictable environmental conditions.

Although examples are illustrated and described herein, embodiments are nevertheless not limited to the details shown, since various modifications and structural changes may be made therein by those of ordinary skill within the scope and range of equivalents of the claims.

What is claimed is:

1. A system for monitoring storage conditions in containers comprising:

a container housing an aircraft engine, an aircraft engine subsystem of the aircraft engine, or both the aircraft engine and the aircraft engine subsystem;

a sensing component positioned within the container housing the aircraft engine, the aircraft engine subsystem of the aircraft engine, or both the aircraft engine and the aircraft engine subsystem, the sensing component comprising:

one or more sensors for sensing atmospheric data in or around the aircraft engine, the aircraft engine subsystem of the aircraft engine, or both the aircraft engine and the aircraft engine subsystem;

a sensing component battery; and a sensing component microcontroller having a memory, wherein the sensing component microcontroller receives the atmospheric data sensed by the one or more sensors at a predetermined interval and stores the atmospheric data in said memory;

a communication chip; and a transmission device that is paired with the sensing component and a unique identifier of the aircraft engine, the transmission device comprising:

a receiver for receiving data and the unique identifier of the aircraft engine transmitted by said sensing component; and a transmitter for transmitting the received data and the unique identifier of the aircraft engine to a storage location, wherein the container housing further includes at least one rail arranged within the container housing and configured to secure the aircraft engine, the aircraft engine subsystem of the aircraft engine, or both the aircraft engine and the aircraft engine subsystem within the container housing, and wherein the sensing component is arranged on the at least one rail.

2. The system of claim 1, wherein the one or more sensors sense environmental conditions within the aircraft engine, the aircraft engine subsystem of the aircraft engine, or both the aircraft engine and the aircraft engine subsystem.

3. The system of claim 1, wherein the transmission device further comprises:

a transmission device microcontroller for processing the received data;

one or more transmission device antennas for wireless communication;

an onboard memory component for storage of the received data; and a transmission device battery.

4. The system of claim 1 wherein the container housing comprises a first removably coupled portion and a second removably coupled portion configured to be removably coupled to the first removably coupled portion, and wherein said sensing component is mounted within a first interior space of the first removably coupled portion and said transmission device is mounted on an external surface of the second removably coupled portion so as to enable the sensing component to monitor separation of the first and second removably coupled portions from each other.

5. The system of claim 1, wherein the storage location is a cloud storage location.

6. The system of claim 1, wherein the container housing is hermetically sealed.

7. The system of claim 1, wherein the transmission device is configured to query the sensing component to effect transmission of atmospheric data.

8. The system of claim 1, wherein the sensing component periodically transmits atmospheric data to the transmission device.

9. The system of claim 1, wherein the unique identifier of the aircraft engine is a serial number of the aircraft engine.

10. A method for monitoring an environment within an interior compartment defined by a container, the method comprising:

providing a container housing an aircraft engine, an aircraft engine subsystem of the aircraft engine, or both the aircraft engine and the aircraft engine subsystem;

positioning a sensing component in the container housing the aircraft engine, the aircraft engine subsystem of the aircraft engine, or both the aircraft engine and the aircraft engine subsystem, the sensing component comprising:

one or more sensors for sensing atmospheric data;

a sensing component battery;

a sensing component microcontroller having a memory, wherein the sensing component microcontroller receives the atmospheric data sensed by the one or more sensors at a predetermined interval and stores the atmospheric data in said memory; and a communication chip;

sensing one or more environmental conditions within the container housing the aircraft engine, the aircraft engine subsystem of the aircraft engine, or both the aircraft engine and the aircraft engine subsystem, by the sensing component to detect damage to the aircraft engine or the aircraft engine subsystem or to detect conditions comprising a physical shock which have damaged the aircraft engine or the aircraft engine subsystem;

positioning a transmitting component proximate the container, the transmitting component being paired with the sensing component and a unique identifier of the aircraft engine; and transferring data related to the one or more environmental conditions and the unique identifier of the aircraft engine between the sensing component and the transmitting component, wherein the container housing further includes at least one rail arranged within the container housing and configured to secure the aircraft engine, the aircraft engine subsystem of the aircraft engine, or both the aircraft engine and the aircraft engine subsystem within the container housing, and wherein the sensing component is arranged on the at least one rail.

11. The method of claim 10, comprising:

transmitting a query from the transmitting component to the sensing component; and responsive to the query, transferring data related to the one or more environmental conditions and the unique identifier of the aircraft engine from the sensing component to the transmitting component.

12. The method of claim 11, wherein the query is transmitted on a predetermined schedule.

13. The method of claim 11, wherein the transmitting component stores the data.

14. The method of claim 13, wherein the transmitting component transmits the data to a receiver remote from the transmitting component.

15. The method of claim 10, wherein the data is related to one or more of temperature, humidity, movement, and light.

16. The method of claim 10, further comprising assigning a serial number to the aircraft engine as the unique identifier.

17. The system of claim 1, wherein the container housing comprises a first removably coupled portion and a second removably coupled portion configured to be removably coupled to the first removably coupled portion, wherein the second removably coupled portion is configured to be arranged on top of the first removably coupled portion, and wherein the aircraft engine, the aircraft engine subsystem of the aircraft engine, or both the aircraft engine and the aircraft engine subsystem is arranged partially within the first removably coupled portion and partially within the second removably coupled portion.

18. The system of claim 1, wherein the container housing comprises a first removably coupled portion defining a first interior space and a second removably coupled portion defining a second interior space and configured to be removably coupled to the first removably coupled portion, wherein the at least one rail is arranged within the first interior space of the first removably coupled portion and configured to secure the aircraft engine, the aircraft engine subsystem of the aircraft engine, or both the aircraft engine and the aircraft engine subsystem within the first interior space, and wherein the at least one rail does not extend into the second interior space of the second removably coupled portion.

* * * * *